United States Patent
Kappel et al.

(10) Patent No.: US 9,943,228 B2
(45) Date of Patent: Apr. 17, 2018

(54) FUNCTIONAL SKIN PATCH

(71) Applicant: Infineon Technologies AG, Neubiberg (DE)

(72) Inventors: Robert Kappel, Graz (AT); Thomas Herndl, Biedermannsdorf (AT); Gerald Holweg, Graz (AT); Walther Pachler, Graz (AT)

(73) Assignee: Infineon Technologies AG, Neubiberg (DE)

( * ) Notice: Subject to any disclaimer, the term of this patent is extended or adjusted under 35 U.S.C. 154(b) by 217 days.

(21) Appl. No.: 14/938,416

(22) Filed: Nov. 11, 2015

(65) Prior Publication Data
US 2016/0135684 A1 May 19, 2016

(30) Foreign Application Priority Data
Nov. 12, 2014 (DE) .................. 10 2014 116 537

(51) Int. Cl.
*H01Q 1/27* (2006.01)
*A61B 5/00* (2006.01)
(Continued)

(52) U.S. Cl.
CPC ........ *A61B 5/0015* (2013.01); *A61B 5/02055* (2013.01); *H01L 35/32* (2013.01);
(Continued)

(58) Field of Classification Search
CPC ........ H01Q 1/273; H01Q 1/2208; H01Q 1/27; A61B 5/0015; A61B 5/02055;
(Continued)

(56) References Cited

U.S. PATENT DOCUMENTS

| 6,632,216 B2* | 10/2003 | Houzego ............... A61M 25/01 604/890.1 |
| 9,042,997 B2* | 5/2015 | Rahman ............... A61N 1/3718 607/60 |

(Continued)

OTHER PUBLICATIONS

Dalola, Simone et al., "Autonomous Sensor System With Power Harvesting for Telemetric Temperature Measurements of Pipes", IEEE Transactions on Instrumentation and Measurement, vol. 58, No. 5, May 2009, pp. 1471-1478.
(Continued)

*Primary Examiner* — Hoang Nguyen
*Assistant Examiner* — Awat Salih
(74) *Attorney, Agent, or Firm* — Murphy, Bilak & Homiller, PLLC

(57) ABSTRACT

A functional skin patch having a first surface and a second surface opposite the first surface is provided. The functional skin patch includes a functional unit having a thermo harvester and an antenna unit. The thermo harvester has a first terminal thermally connected to the first surface and a second terminal. The antenna unit has a first terminal thermally connected to the second terminal of the thermo harvester and a second terminal thermally connected to the second surface. The antenna unit has a stacked layer structure including, in this sequence, a metal layer thermally connected to the second terminal of the thermo harvester, a ferrite layer thermally connected to the metal layer, and an antenna layer thermally connected to the ferrite layer.

20 Claims, 9 Drawing Sheets

(51) Int. Cl.
  *H01L 35/32* (2006.01)
  *A61B 5/0205* (2006.01)
  *H01Q 1/22* (2006.01)
  *H01Q 7/00* (2006.01)
  *A61B 5/01* (2006.01)
  *A61B 5/024* (2006.01)
  *A61B 5/021* (2006.01)
  *A61B 5/0476* (2006.01)
  *A61B 5/145* (2006.01)

(52) U.S. Cl.
  CPC .......... *H01Q 1/2208* (2013.01); *H01Q 1/273* (2013.01); *H01Q 7/00* (2013.01); *A61B 5/021* (2013.01); *A61B 5/024* (2013.01); *A61B 5/0476* (2013.01); *A61B 5/14532* (2013.01); *A61B 5/14546* (2013.01); *A61B 2560/0214* (2013.01); *A61B 2560/0219* (2013.01)

(58) Field of Classification Search
  CPC ....... A61B 5/021; A61B 5/024; A61B 5/0476; A61B 5/14532; A61B 5/15546; A61B 2560/0214; A61B 2560/0219; H01L 35/32
  See application file for complete search history.

(56) References Cited

U.S. PATENT DOCUMENTS

| | | | |
|---|---|---|---|
| 2002/0084880 A1* | 7/2002 | Barbera-Guilem | B03C 1/288 336/200 |
| 2004/0193020 A1 | 9/2004 | Chiba et al. | |
| 2006/0195161 A1* | 8/2006 | Li | A61N 1/37223 607/60 |
| 2006/0267200 A1* | 11/2006 | Mickle | G06K 19/07749 257/754 |
| 2011/0032156 A1* | 2/2011 | Sugiyama | H01Q 1/243 343/700 MS |
| 2013/0110195 A1* | 5/2013 | Fletcher | A61N 1/36075 607/46 |
| 2013/0116745 A1* | 5/2013 | Fletcher | A61N 1/36075 607/46 |
| 2013/0234899 A1* | 9/2013 | Pope | H01Q 1/243 343/702 |
| 2013/0293430 A1* | 11/2013 | Henty | H01F 38/14 343/720 |
| 2013/0296723 A1* | 11/2013 | Cho | A61B 5/02108 600/501 |
| 2014/0020728 A1* | 1/2014 | Chung | H01L 35/32 136/205 |
| 2014/0110402 A1* | 4/2014 | Clemen, Jr. | H05K 3/22 219/672 |
| 2014/0320365 A1* | 10/2014 | Hong | H01Q 1/38 343/787 |
| 2015/0123860 A1* | 5/2015 | Park | H01Q 1/22 343/720 |
| 2015/0351292 A1* | 12/2015 | Chang | H01Q 1/526 361/749 |

OTHER PUBLICATIONS

Pachler, Walther et al., "A Silver Inkjet Printed Ferrite NFC Antenna", Loughborough Antennas and Propagation Conference (LAPC), Nov. 2014, pp. 95-99.

Virili, Marco et al., "Design and Optimization of an Antenna with Thermo-Electric Generator (TEG) for Autonomous Wireless Nodes", IEEE RFID Technology and Applications Conference (RFID-TA), Sep. 2014, pp. 21-26.

\* cited by examiner

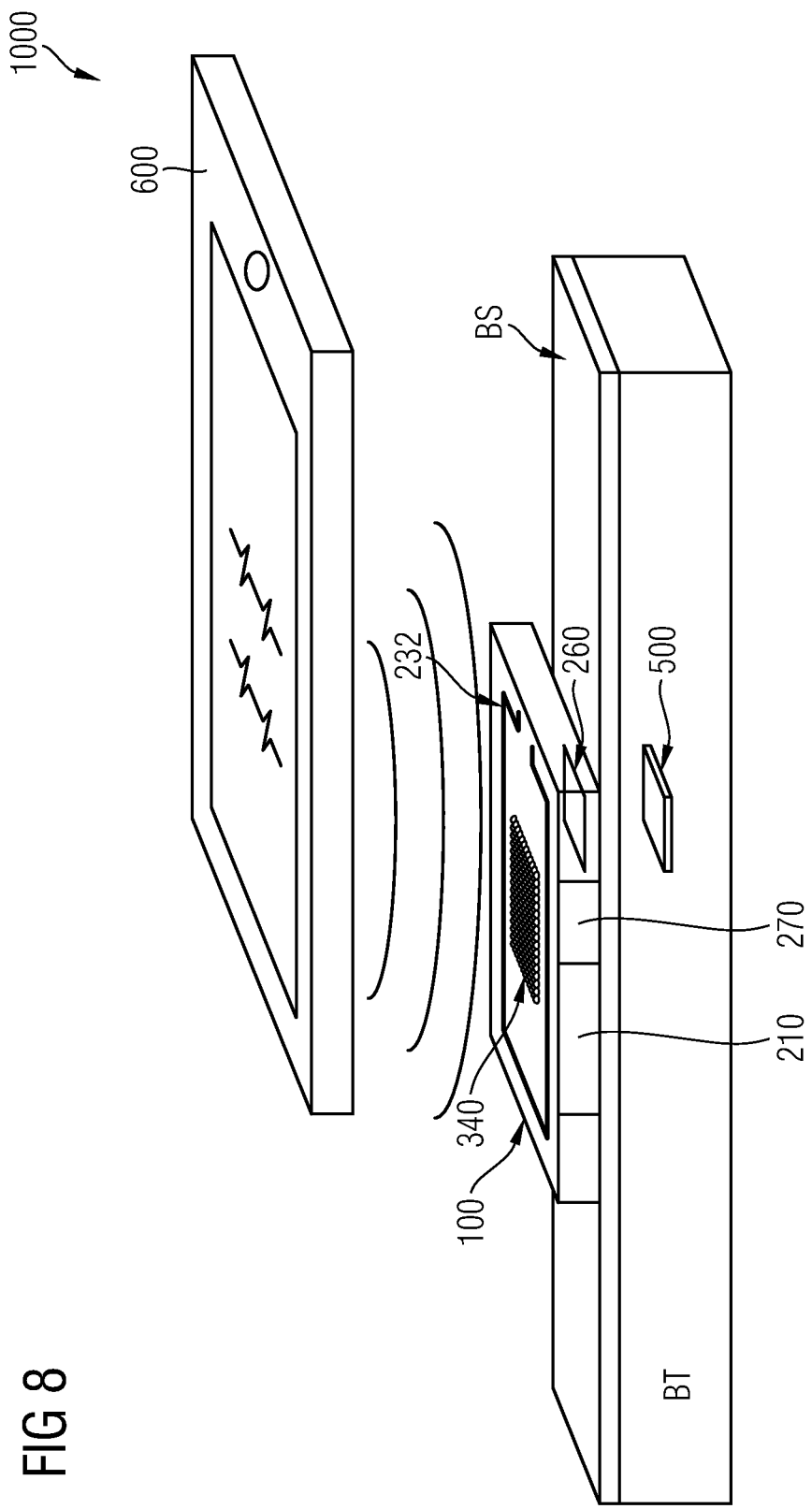

FUNCTIONAL SKIN PATCH

PRIORITY CLAIM

This application claims priority to German Patent Application No. 10 2014 116 537.3 filed on 12 Nov. 2014, the content of said application incorporated herein by reference in its entirety.

BACKGROUND

Functional skin patches or sensor plasters for medical or industrial monitoring networks provide limited space in a thickness direction and further require flexibility to fit to the underlying body, e.g. a human body. In case a thermo harvester is integrated in a functional skin patch, a radiating surface of maximized area is desirable to enhance the thermal conductivity between the functional skin patch and the surrounding air. To provide a low thermal transfer resistance of the outer surface of the functional skin patch, a metal layer may be provided. However, in case the functional skin patch is equipped with an antenna unit, the radiating outer surface and the antenna part compete for the surface area of the outer surface of the functional skin patch.

It is an object to provide a functional skin patch having an antenna and improved thermo harvesting properties.

SUMMARY

According to an embodiment of a functional skin patch having a first surface and a second surface opposite the first surface, the functional skin patch comprises a functional unit comprising a thermo harvester, the thermo harvester having a first terminal thermally connected to the first surface and a second terminal, and an antenna unit having a first terminal thermally connected to the second terminal of the thermo harvester and a second terminal thermally connected to the second surface, wherein the antenna unit has a stacked layer structure comprising, in this sequence, a metal layer thermally connected to the second terminal of the thermo harvester, a ferrite layer thermally connected to the metal layer, and an antenna layer thermally connected to the ferrite layer.

According to an embodiment of a system for monitoring a body health parameter, the system comprises a functional skin patch, and an implantable device having a sensor unit for measuring at least one body health parameter, a data transceiver unit for transmitting measurement data containing the at least one body health parameter to the functional skin patch, and an energy receiving unit for receiving electromagnetic energy from the coupling antenna of the functional skin patch.

Those skilled in the art will recognize additional features and advantages upon reading the following detailed description and on viewing the accompanying drawings.

BRIEF DESCRIPTION OF THE DRAWINGS

The accompanying drawings are included to provide a further understanding of the invention and are incorporated in and constitute a part of this specification. The drawings illustrate the embodiments of the present invention and together with the description serve to explain principles of the invention. Other embodiments of the invention and intended advantages will be readily appreciated as they become better understood by reference to the following detailed description.

FIG. 8 is a schematic perspective view of a system for monitoring a body health parameter according to an embodiment.

DETAILED DESCRIPTION

In the following detailed description, reference is made to the accompanying drawings, which form a part hereof, and in which are shown by way of illustrations specific embodiments in which the invention may be practiced. It is to be understood that other embodiments may be utilized and structural or logical changes may be made without departing from the scope of the present invention. For example, features illustrated or described for one embodiment can be used on or in conjunction with other embodiments to yield yet a further embodiment. It is intended that the present invention includes such modifications and variations. The examples are described using specific language which should not be construed as limiting the scope of the appending claims. The drawings are not scaled and are for illustrative purposes only. For clarity, the same elements have been designated by corresponding references in the different drawings if not stated otherwise.

The terms "having", "containing", "including", "comprising" and the like are open and the terms indicate the presence of stated structures, elements or features but not preclude additional elements or features. The articles "a", "an" and "the" are intended to include the plural as well as the singular, unless the context clearly indicates otherwise.

The term "electrically connected" describes a permanent low-ohmic connection between electrically connected elements, for example a direct contact between the concerned elements or a low-ohmic connection via a metal and/or highly doped semiconductor. The term "electrically coupled" includes that one or more intervening element(s) configured for signal transmission may be provided between the electrically coupled elements, for example resistors, resistive elements or elements that are controllable to temporarily provide a low-ohmic connection in a first state and a high-ohmic electric decoupling in a second state.

Figure 1A:
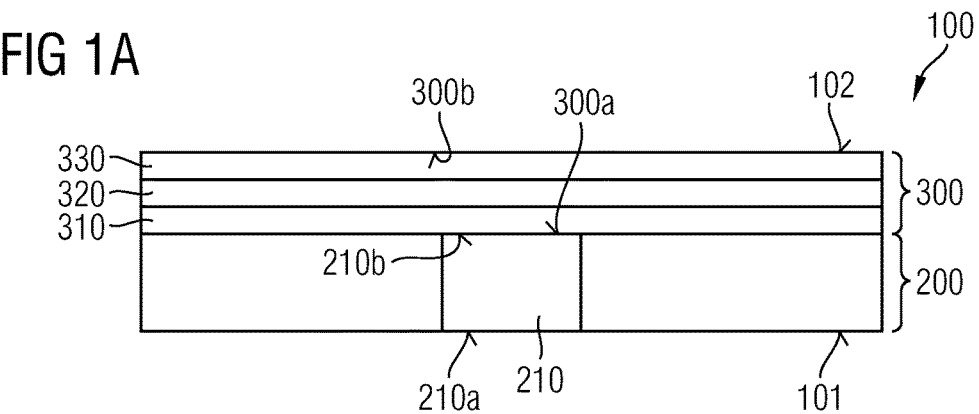
FIG. 1A is a schematic block diagram of a functional skin patch according to an embodiment.

FIG. 1A is a schematic block diagram of a functional skin patch 100 according to an embodiment. As can be seen from FIG. 1A, the functional skin patch 100 has a first surface 101 and a second surface 102, which is opposite to the first surface 101. The functional skin patch 100 comprises a functional unit 200 and an antenna unit 300. The functional unit 200 comprises a thermo harvester 210, wherein the thermo harvester 210 has a first terminal 210a thermally connected to the first surface 101 and a second terminal 210b. The second terminal 210b of the thermo harvester 210 is thermally connected to a first terminal 300a of the antenna unit 300. A second terminal 300b of the antenna unit 300 is thermally connected to the second surface 102. The antenna unit 300 has a stacked layer structure comprising, in this sequence, a metal layer 310 thermally connected to the second terminal 210b of the thermo harvester 210, a ferrite layer 320 thermally connected to the metal layer 310, and an antenna layer 330 thermally connected to the ferrite layer 320.

By providing the structure of the functional skin patch 100, an electromagnetic field of the antenna layer 330 is reflected by the ferrite layer 320 while at the same time the antenna layer 330 is electrically isolated from the metal layer 310. As a consequence, by providing the antenna unit 300 having the stacked layer structure of the metal layer 310, the ferrite layer 320 and the antenna layer 330, an excellent heat flux from the second terminal 210b of the thermo harvester 210 to the second surface 102 of the functional skin patch 100 may be provided while the functionality of the antenna layer 330 is not negatively affected.

Figure 1B:
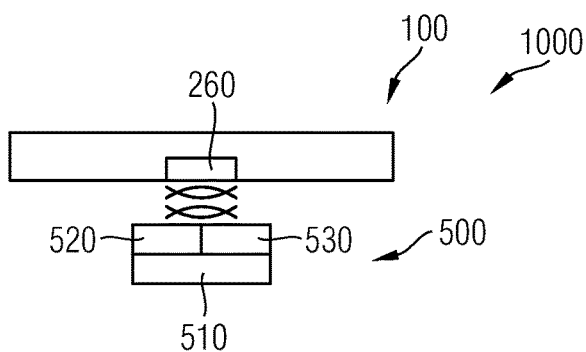
FIG. 1B is a schematic block diagram of a system for monitoring a body health parameter according to an embodiment.

FIG. 1B is a schematic block diagram of a system 1000 for monitoring a body health parameter according to an embodiment. The system 1000 comprises a functional skin patch 100 and an implantable device 500. The implantable device 500 has a sensor unit 510 for measuring at least one body health parameter, a data transceiver unit 520 for transmitting measurement data containing the at least one body health parameter to the functional skin patch 100, and an energy receiving unit 530 for receiving electromagnetic energy from the coupling antenna 260 of the functional skin patch 100.

By providing the system 1000 as shown in FIG. 1B, an implantable device may be energized by the functional skin patch 100, which in turn is configured to generate autonomously energy by means of the thermo harvester 210. Thus, a long term monitoring of at least one body health parameter may be achieved, wherein the energy for the monitoring is at least partly generated by harvesting the body heat.

Figure 2:
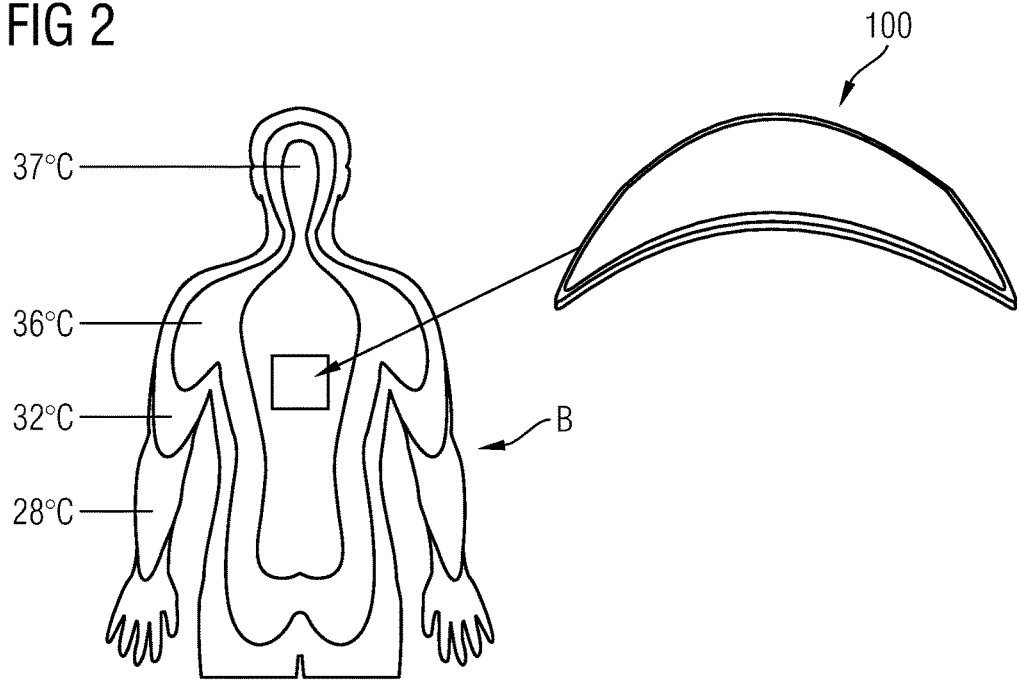
FIG. 2 illustrates an arrangement position on a human body of a functional skin patch according to an embodiment.

FIG. 2 illustrates and arrangement position of a functional skin patch 100 on a human body B. The functional skin patch 100 according to an embodiment is configured to harvest the body heat by conducting heat from a body skin through the thermo harvester 210 to an outer surface, i.e. the second surface 102, which is in contact with the air of the environment. The application of the functional skin patch 100 is not restricted to the human body B, but it is also possible to apply the functional skin patch 100 to a body surface of an animal, which is preferably an endotherm. As can be seen from FIG. 2, the extremities of the human body B have a lower temperature, thus an application at the torso of the human body B is preferred. The temperature of the human body B reaches from a temperature range of 28° C. at a forearm region to 37° C. at a torso region of the human body B.

The area of the first and second surface 101, 102 of the functional skin patch 100 may be in a range of 20 cm$^2$ to 500 cm$^2$, or in a range of 50 cm$^2$ to 100 cm$^2$, or in a range of 50 cm$^2$ to 80 cm$^2$. The size of the functional skin patch 100 is a trade-off between the amount of heat which can be harvested, and the convenience for a person wearing the functional skin patch 100.

Figure 3:
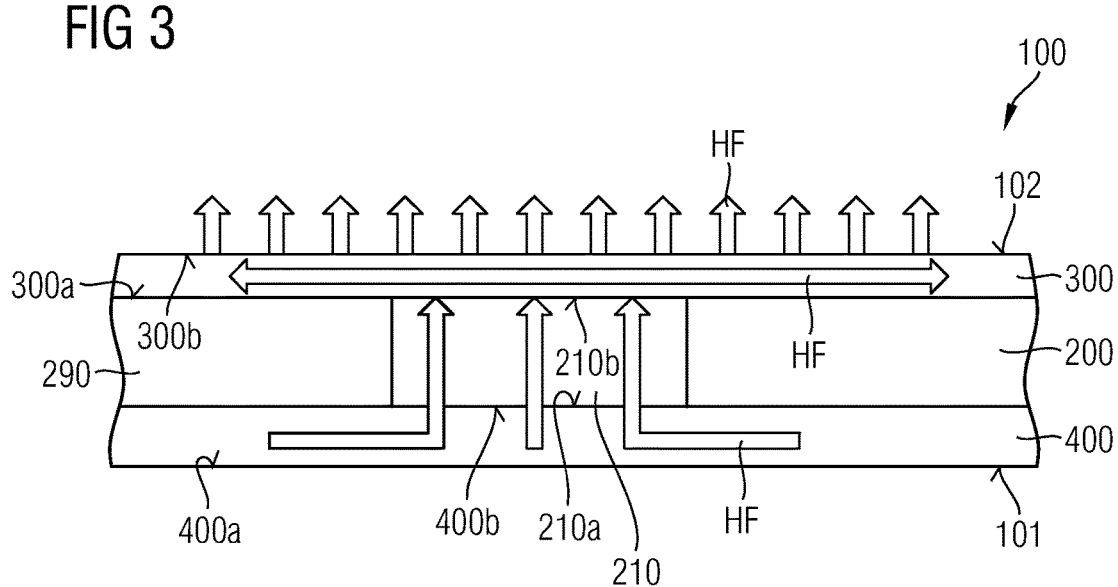
FIG. 3 is a schematic diagram illustrating heat flow through the functional skin patch according to an embodiment.
Figure 4:
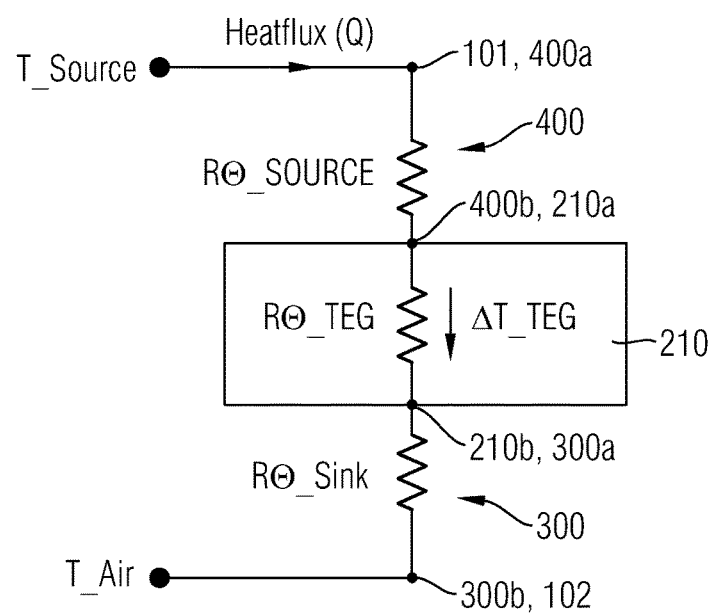
FIG. 4 is a thermal circuit diagram illustrating the heat flux through the functional skin patch according to an embodiment.

FIG. 3 illustrates the heat flux within the functional skin patch 100 according to an embodiment, wherein FIG. 4 is the corresponding thermal circuit diagram of the functional skin patch 100. As can be seen from FIG. 3, the functional skin patch 100 may further comprise a heat collector unit 400 having a first terminal 400a thermally connected to the first surface 101 and a second terminal 400b thermally connected to the first terminal 210a of the thermo harvester 210. As further illustrated in FIG. 3, the thermo harvester 210 may be embedded in a thermally isolating layer 290, to ensure that the heat flux is guided only through the thermo harvester 210 and is not bypassed or shunted from the heat collector unit 400 to the antenna unit 300. The thermally isolating layer 290 may comprise at least one of wool, cellulose, foamed plastics such as expanded polyethylene or a material which fulfils the requirements of being flexible and at the same time having a low heat conductance. The thermal resistance of the thermally isolating layer 290 may be in a range of 20 to 50 K/W.

The heat flux Q flows, as shown in FIG. 4, from the skin of a body, which has a temperature T_source, via the first surface 101, the first terminal 400a of the heat collector unit 400, and the second terminal 400b to the heat collector unit 400 having a thermal resistance Rθ_source. From the second terminal 400b of the heat collector unit 400, the heat flux Q flows through the thermal harvester 210 from the first terminal 210a to the second terminal 210b, wherein the inner thermal resistance of the thermo harvester 210 is Rθ_TEG. The heat is then guided from the second terminal 210b of the thermo harvester 210 through the antenna unit 300 having a thermal resistance of Rθ_sink and from the first terminal 300a to the second terminal 300b of the antenna unit 300. At least, the heat is then radiated from the second surface 102 being in contact with air having the temperature T_Air, wherein the second surface 102 is in thermal contact with the second terminal 300b of the antenna unit 300.

Thermoelectric energy harvesting of the thermo harvester 210 makes use of the thermo electric effect to gain electric energy from a temperature difference ΔT_TEG. In an operating state of the thermo harvester 210, a continuous heat flux occurs from the heat source having the temperature T_source through the thermo harvester 210 via the radiating second surface 102 to the surrounding air having the temperature T_Air. A crucial parameter in the described system is the thermal transfer resistance of the second terminal 300b of the antenna unit 300 or the second surface 102 to the surrounding air. In case no sufficient heat radiation occurs, the temperature at the second terminal 210b of the thermo harvester 210 rises, thus the temperature gradient ΔT_TEG will be diminished, resulting in a lower output power of the thermo harvester 210. As a consequence, the thermal resistance of the heat collector unit 400 Rθ_source and the thermal resistance of the antenna unit 300 Rθ_sink is preferably low to reduce the thermal resistive impedance drop at the respective thermal resistors of the antenna unit 300 and the heat collector unit 400.

Thus, the heat collector unit 400 is preferably made of a material having a high thermal conductivity such as a metal or a material having a sufficient flexibility and at the same time a high thermal conductivity. In an analogous way, the antenna unit 300 being configured to spread the heat flux from the second terminal 210b of the thermo harvester 210 to the second surface 102 is made of a material or a material composition having a low thermal resistance. From a heat conductance side of view, an antenna unit 300 consisting only of a material having a high thermal conductivity may be preferred. However, most of the materials with a sufficient flexibility and a high thermal conductivity show at the same time a high electric conductivity.

Thus, for providing an antenna structure, which is not shunted by the antenna unit 300 and which may be selectively contacted from the side of the functional unit 200, a design of the antenna unit 300 is necessary, which provides both the possibility of having an antenna structure and improved thermal conductance properties. In other words, a co-integration of an antenna and a heat sink has to be provided, which has a small size and a flexible design. Herein, the antenna unit 300 should combine the properties of an ideal heat sink being a good heat conductor, having a large surface area and being flexible, and of an ideal antenna substrate being an electrical insulator.

The temperature T_source of the skin is lowered by the thermal resistance of the skin, thus a region, in which the body temperature is about 37° C., is lowered to a temperature of about 28° C. to 30° C. In case the temperature of the environment T_air is about 10° C. to 15° C., a total temperature difference between T_source and T_air is in a range of 10° C. Taking into account the thermal resistances Rθ_source and Rθ_sink, a temperature difference ΔT_TEG over Rθ_TEG is in a range of 1 K to 3 K. The power density of the human body B in the torso region is about 3.5 mW/cm². Rθ_source may be in a range of 10 K/W-300 K/W. (Rθ_source includes the complete thermal resistance from the inner part of the body to the thermo harvester). Rθ_TEG may be in a range between 10 K/W and 20 K/W. Rθ_sink may be in a range of 100 K/W to 300 K/W, or in a range of 100 K/W to 120 K/W, as will be discussed below.

Figure 5A:
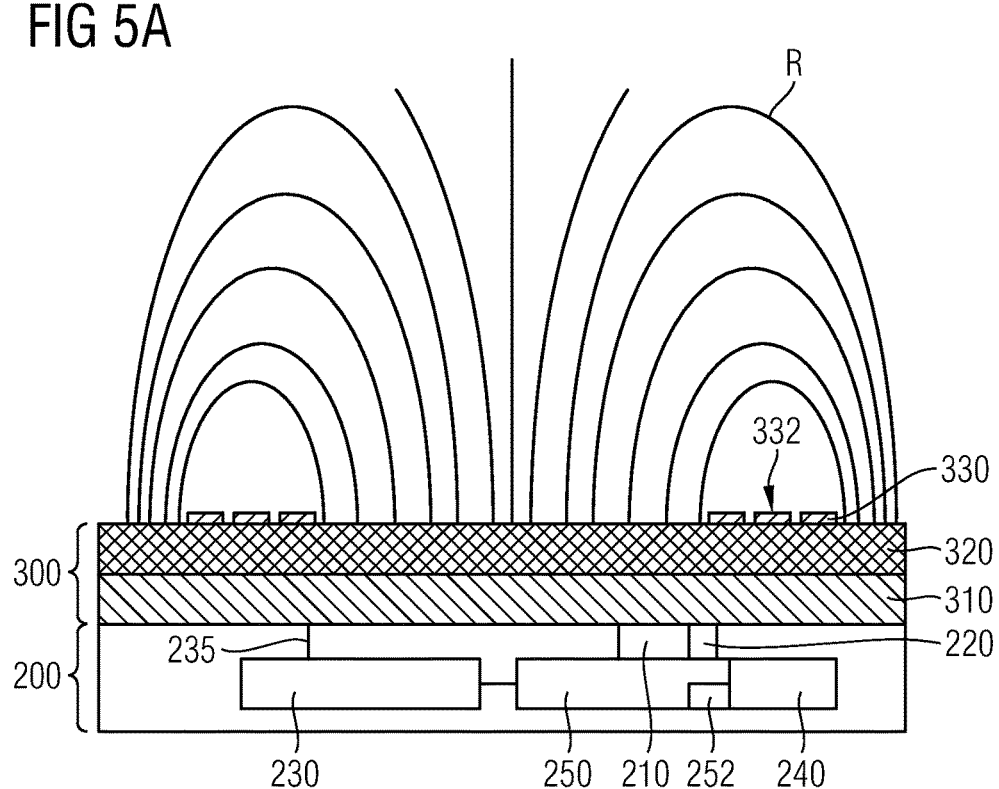
FIG. 5A is a schematic cross-sectional view of a portion of a functional skin patch according to an embodiment.

FIG. 5A is a schematic cross-sectional view of a portion of a functional skin patch 100 of an embodiment.

Figure 5B:
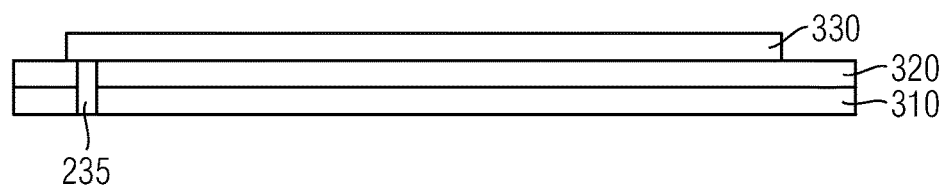
FIG. 5B is a schematic cross-sectional view of a portion of the antenna unit of the functional skin patch according to an embodiment.
Figure 6:
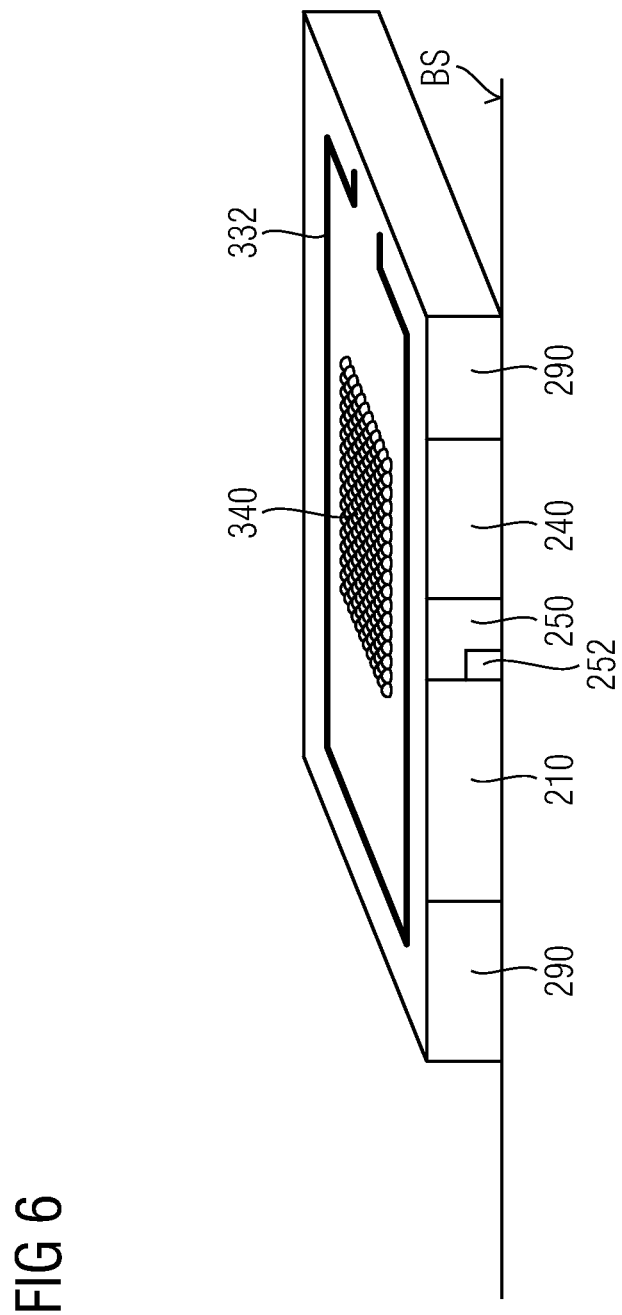
FIG. 6 is a schematic perspective view of a functional skin patch comprising a metal dot layer printed on a ferrite layer for enhancing the surface area of the antenna layer according to an embodiment.

As can be seen from FIG. 5A, the functional unit 200 comprises, next to the thermo harvester 210, further functional elements. The functional unit 200 may further comprise a radio frequency (RF) circuit 230, which is connected to the antenna layer 330 via a connection plug 235. The connection plug 235 is, as can be seen from FIG. 5B, extended through the metal layer 310 and the ferrite layer 320 and connected to the antenna layer 330. FIG. 5B is a detailed view of the antenna unit 300. The transmission frequency of the RF-circuit 230 and of the antenna layer 330 is in a range, which is configured to the size of the functional skin patch 100. Preferably, the transmission band is in a range of 10 MHz to 100 MHz, or in a range of 10 MHz to 50 MHz, or in a range of 10 MHz to 20 MHz, or in a range of 13 MHz to 14 MHz.

The functional unit 200 may further comprise a sensor unit 240, which is configured to sense a body health parameter including at least one of a body temperature, a body pulse frequency, an electrocardiogram recording, an electroencephalogram recording, a body function, a blood sugar value, a blood pressure, or a blood heparin value. The body temperature may be measured by an integrated thermometer. The body pulse frequency, the electrocardiogram recording, and the electroencephalogram recording may be measured by electrodes integrated in the first surface 101 of the functional skin patch 100, wherein the measured electrode potential recording is analysed in a well-known manner. Furthermore, a blood sugar value may be measured invasively by a sensor chip analysing blood or interstitial fluid composition or non-invasively by near infrared or infrared recording or by photoacoustic measurements of the interstitial fluid in the subcutaneous tissue. In addition, a blood pressure may be measured directly by the functional skin patch 100 or by use of an implanted device, as will be discussed below. The blood heparin value may be measured invasively or non-invasively by the functional skin patch 100 in an analogous way as the blood sugar value.

The thermo harvester 210 may comprise an energy storage unit 220 for storing the harvested body energy. The energy storage unit 220 may be a rechargeable battery or a capacitor being configured to store sufficient energy for providing a long term monitoring of the body health parameters. The size of the energy storage unit 220 is only limited by the thickness of the functional unit 200. To provide an energy storage unit 220 having a low thickness, printed energy storage devices or printed supercapacitors may be used.

Further, the functional unit 200 may comprise a processing unit 250 for processing measurement data of the sensor unit 240 and for transmitting the measurement data to the RF-circuit 230. The processing unit 250 may be integrated in a monolithic circuit. Thus, at least one body health parameter may be measured by the sensor unit 240 and transmitted to the processing unit 250, which processes or analyses the measurement data of the sensor unit 240. The processed measurement data is then transmitted from the processing unit 250 to the RF-circuit 230. The RF-circuit 230 generates a radio frequency (RF) signal modulated by the measurement data information and transmits the RF-signal via the connection plug 235 to the antenna layer 330. As can be seen from FIG. 5A, the RF-signal is then radiated from the antenna layer 330 to be received by an external receiver to receive the measurement data from the sensor unit 240. The RF-circuit 230 may also be configured to receive RF-signals from an external transceiver to receive instructions for operating the functional unit 200.

As can be seen from FIGS. 5A and 5B, the metal layer 310 may be a flexible metal foil having a thickness in a range between 5 μm and 1000 μm. The thickness of the metal layer 310 may be also in a range between 5 μm to 300 μm, or in a range of 50 μm to 100 μm. The flexible metal foil may comprise copper to optimally spread the heat energy over the complete surface of the functional skin patch 100.

Figure 7A:
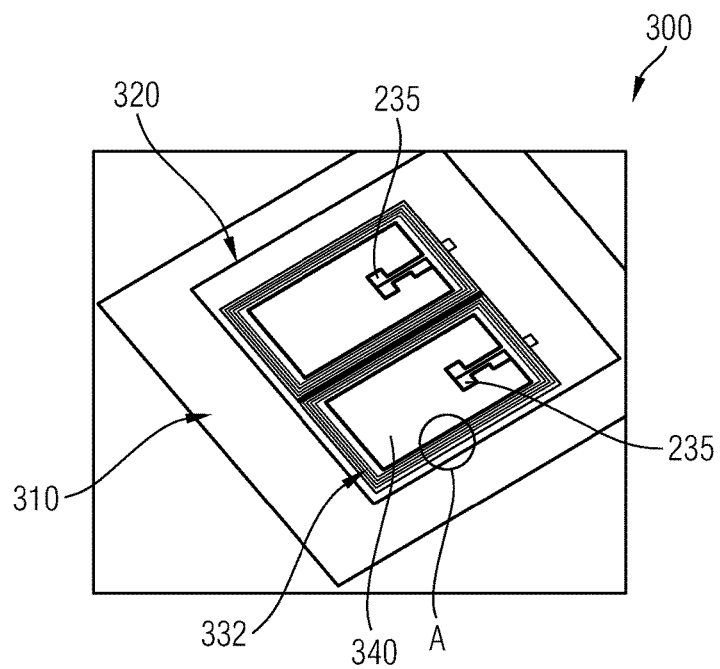
FIG. 7A is a schematic perspective view of the antenna unit according to an embodiment.
Figure 7B:
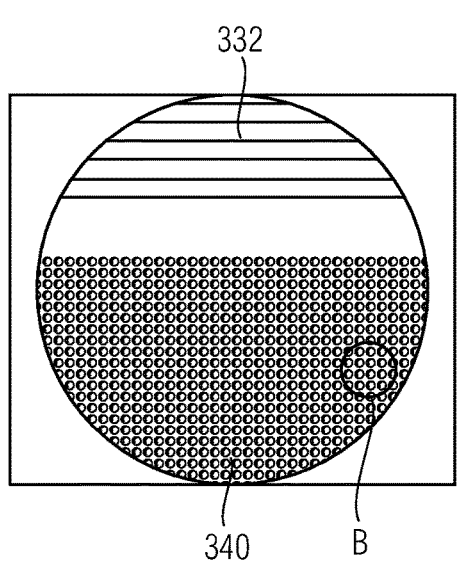
FIG. 7B is a detailed view of the part A of FIG. 7A showing an antenna pattern and a metal dot layer printed on the ferrite layer of the functional skin patch according to an embodiment.
Figure 7C:
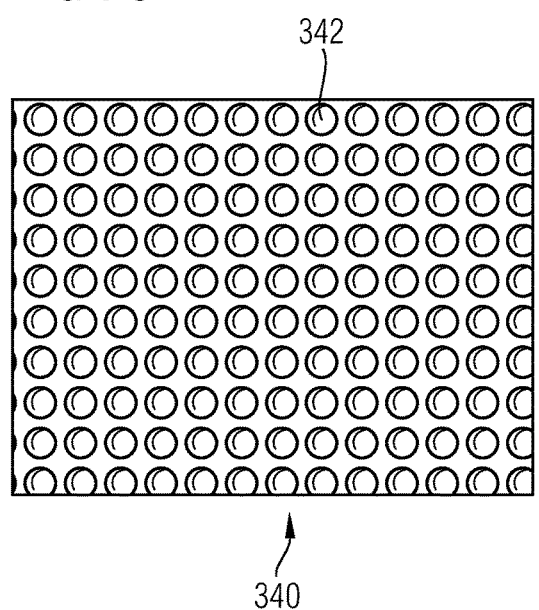
FIG. 7C is a detailed view of the part B of FIG. 7B showing the metal dot layer printed on the ferrite layer.

The ferrite layer 320 may be a flexible ferrite foil having a thickness in a range between 5 μm and 1000 μm. The thickness of the ferrite layer 320 may also have, comparable to the metal layer 310, a thickness in a range between 5 μm to 300 μm or in a range between 50 μm to 100 μm. The flexible ferrite foil of the ferrite layer 320 is configured to shield the RF-field of the antenna 332, as can be seen from FIG. 5A. Ferrite foils are electrical isolators and have a relatively high heat conductivity. In particular, in case of a small thickness of lower than 100 μm a good heat transfer may be achieved to the environment of air. The ferrite layer 320 may include a ferrite material such as $Fe_2O_3$ or $Fe_3O_4$, and may further include, for adapting the magnetic properties, MnZn-ferrite such as $Mn_aZn_{(1-a)}Fe_2O_4$, or NiZn-ferrite such as $Ni_aZn_{(1-a)}Fe_2O_4$. The antenna layer 330 includes an antenna pattern 332, which is printed on the ferrite layer 320. The printed antenna patterned may be realized by a silver printing in an inkjet process. Thus, the antenna layer 330 is not a continuous layer but a patterned layer being configured to form an antenna structure, as can be seen, for example in FIG. 7A. The antenna pattern 332 may thus have a form of a loop antenna as used, for example for RF-ID antennas. As can be seen from FIG. 5A, the metal layer 310, the ferrite layer 320 and the antenna layer 330 may be in direct contact with each other to maximize the heat conductance between these three layers.

It has been found that the specific thermal resistance of the stacked layer structure of the metal layer 310 and the ferrite layer 320 is lower than the thermal resistance of the metal layer 310 and the ferrite layer 320 taken alone. This results from the transfer thermal resistance of the metal layer 310 or 320 to the surrounding air. In case only the ferrite layer 320 or the ferrite foil is used, a high thermal transfer resistance results from the low specific heat conductance of ferrite and thus for the lack of sufficient spreading of the heat to the complete second surface 102. In case only a metal layer 310 such as a copper foil is used, the thermal resistance is reduced resulting from the high specific heat conductance of metal and the good spreading properties of the heat over the complete second surface 102. Nonetheless, the surface of the metal foil of the metal layer 310 is very smooth.

The combination of the metal layer 310 and the ferrite layer 320 leads to overall higher heat conductance properties. The metal in the metal foil of the metal layer 310 leads to a good spreading of the heat over the complete second surface 102, wherein the ferrite layer 320 having a thickness of only 50 μm to 300 μm achieves a good radiation of the heat due to its intrinsic surface roughness. The surface roughness of the ferrite layer 320 results in a reduced thermal transfer resistance to the surrounding air.

Taking the example of measuring a thermal resistance of a plaster having a size of 60 mm×90 mm, the thermal resistance of the ferrite layer 320 has been determined to 313.10 K/W and the thermal resistance of the metal foil of the metal layer 310 has been determined to 14.52 K/W. This results in a specific surface thermal resistance of the metal foil of the metal layer 310 of 2.60 K/(W cm$^2$) and of the ferrite layer 320 of 5.79 K/(W cm$^2$). A combination of the metal layer 310 and the ferrite layer 320 having an overall thickness of 300 μm results in a thermal resistance of 108.00 K/W and a specific surface thermal resistance of 2.00 K/(W cm$^2$). Thus, a combination of the metal layer 310 and the ferrite layer 320 leads to a better heat conductance than the metal layer 310 or the ferrite layer 320 taken alone. Reducing the thickness of the stacked layer of the ferrite layer 320 and the metal layer 310 to an overall thickness of 100 μm leads to thermal resistance values of 109.72 K/W and 2.03 K/(W cm$^2$) and the reduction of the thickness of the ferrite/metal layer to 50 μm leads to values of 118.63 K/W and 2.20 K/(W cm$^2$). Thus, the reduction of the overall thickness of the stacked layer structure of the metal layer 310 and the ferrite layer 320 down to even 50 μm still leads to better heat conductance values as the metal layer 310 or the ferrite layer 320 taken alone.

As can be seen from FIG. 6 and FIG. 7A to 7C, the antenna layer 330 may further comprise a metal dot layer 340 printed on the ferrite layer 320 for enhancing the surface area of the antenna layer 330. As can be seen from FIG. 7B and FIG. 7C, the metal dot layer 340 may be printed next to the antenna pattern 332 on the ferrite layer 320, to enhance the surface area of the second surface 102. Therefore, metal dots 342 having a thickness in a range of 1 μm to 10 μm may be printed on the ferrite layer 320. The diameter of the metal dots 342 may also be enhanced to a diameter in a range of 50 μm to 200 μm. However, due to the intrinsic surface roughness of the ferrite layer 320, the application of a metal dot layer 340 may further improve the heat transfer in case the metal dot layer 340 still leaves a sufficient surface area for the ferrite layer 320 being in contact with air. The metal dot layer 340 and the metal dots 342 are produced in a silver inkjet process or may be also generated in a screen printing.

FIG. 8 is a schematic perspective view of a system 1000 for monitoring a body health parameter. The system 1000 comprises the functional skin patch 100 as already described in detail above, but having a further functionality to communicate with an implantable device 500. Therefore, the functional skin patch 100 comprises the coupling antenna 260 for communicating with or energizing the implantable device 500, as will be discussed in detail below. As can be seen from FIGS. 8 and 9, the implantable device 500 may be embedded in the body tissue BT or in an subcutaneous area near to the body skin BS, to achieve communication between the implantable device 500 and the functional skin patch 100. The functional skin patch 100 may have in this embodiment the functionality of a so-called booster-plaster, which receives an external RF-signal from an external transceiver 600 by means of the antenna pattern 332, wherein the external RF-field is amplified or boosted to be sent to the implantable device 500 via the coupling antenna 260. Therefore, the antenna layer 330 may be connected to the coupling antenna 260 to boost transmission from the external transceiver 600 to the implantable device 500.

Figure 9:
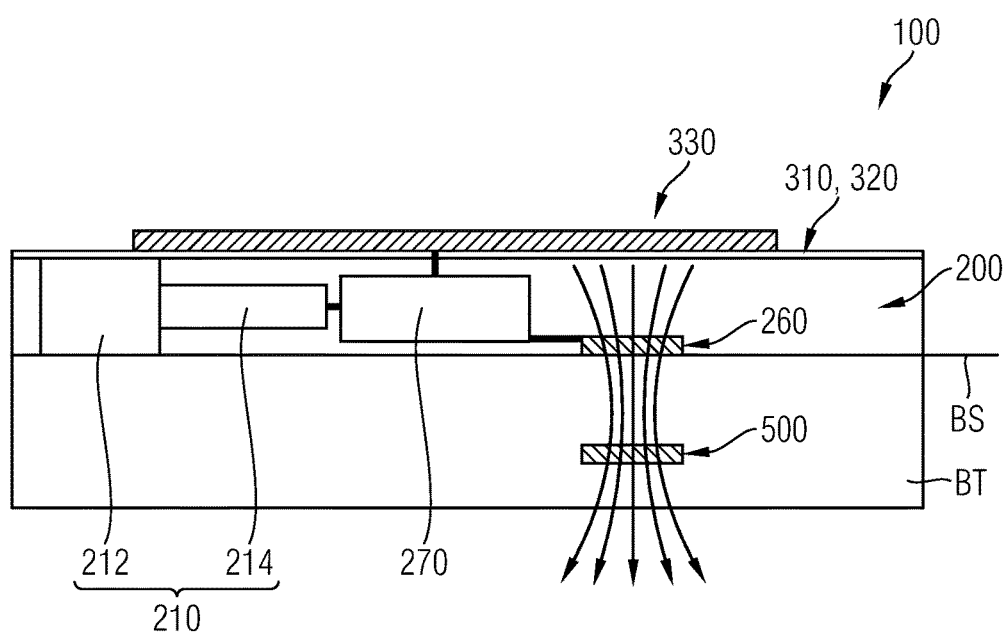
FIG. 9 is a schematic cross-sectional view of a functional skin patch of the system for monitoring a body health parameter according to an embodiment.

As can be seen from FIG. 9, the functional skin patch 100 comprises, comparable to the functional skin patch 100 as shown in FIG. 5A, an antenna layer 330, the ferrite layer 320 and the metal layer 310 as well as the thermo harvester 210 comprising a Peltier element 212, which may include $Bi_2Te_3$, and a harvester circuit 214, which is configured to harvest the thermoelectric energy from the Peltier element 212. Thermoelectric power generation of the thermo harvester 210 may be based on the transfer of thermal energy through multiple couples of p-type and n-type thermoelectric legs. The thermo harvester 210 may use compounds of Bismuth (Bi), Antimony (Sb), Tellurium (Te) and Selenium (Se) providing optimal efficacy at operating temperatures around ambient and up to 85° C. The generated output voltage is proportional to the number of leg pairs and the actual temperature difference ΔT_TEG across the thermo harvester 210. The thermo harvester 210 may have a packing density of up to 100 thermoelectric leg pairs per mm$^2$. As per Seebeck's law this translates into 1.4 V at as little as 10° C. of temperature difference ΔT_TEG. The thermo harvester 210 may have a thickness in a range between 0.2 mm to 5 mm, or 0.5 mm to 2 mm, or 0.5 mm to 1.5 mm. The surface area of the thermo harvester 210 may be in a range of 5 mm$^2$ to 20 mm$^2$, or 5 mm$^2$ to 15 mm$^2$, or 10 mm$^2$ to 15 mm$^2$. The total number of leg pairs may be in a range between 200 and 1000, or between 300 and 600. The output voltage may be in a range between 100 mV/K to 200 mV/K. In addition, the functional unit 200 may further comprise an energizing unit 270, which is configured to energize the implantable device 500 via the coupling antenna 260.

The implantable device 500 may have the sensor unit 510 for measuring at least one body health parameter, the data transceiver unit 520 for transmitting measurement data containing the at least body health parameter to the functional skin patch 100, and the energy receiving unit 530 for receiving electromagnetic energy from the coupling antenna

Figure 10A:
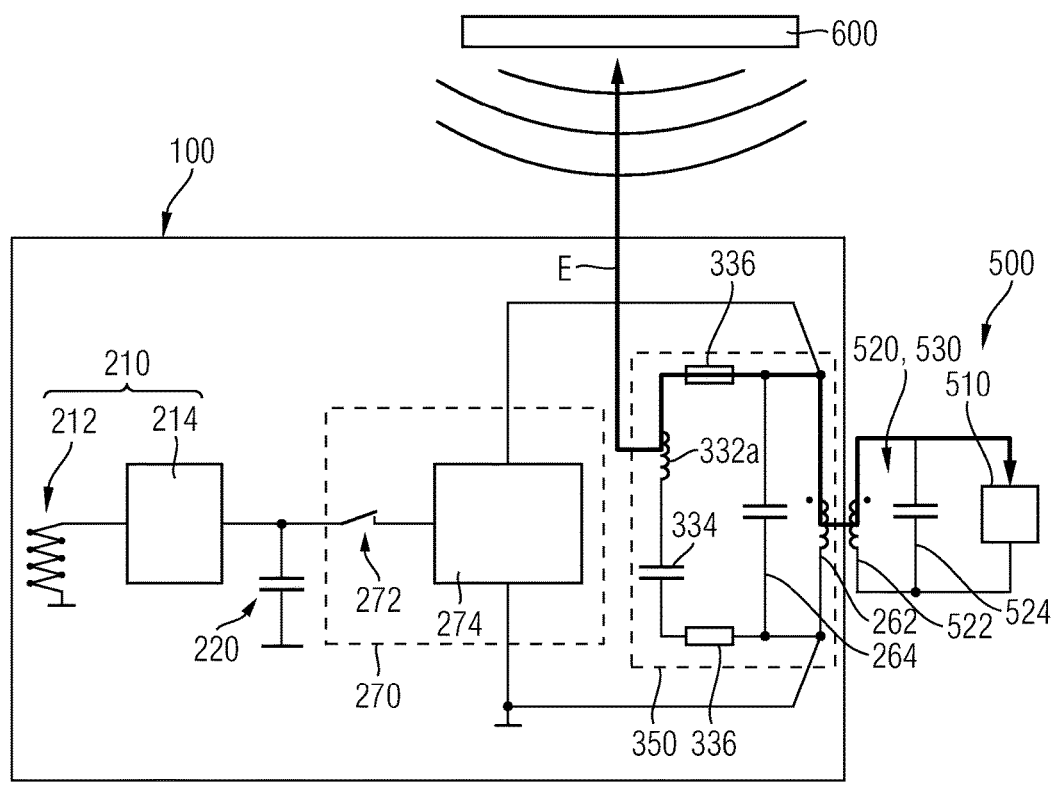
FIG. 10A is a schematic circuit diagram of the system for monitoring a body health parameter in a first modus.
Figure 10B:
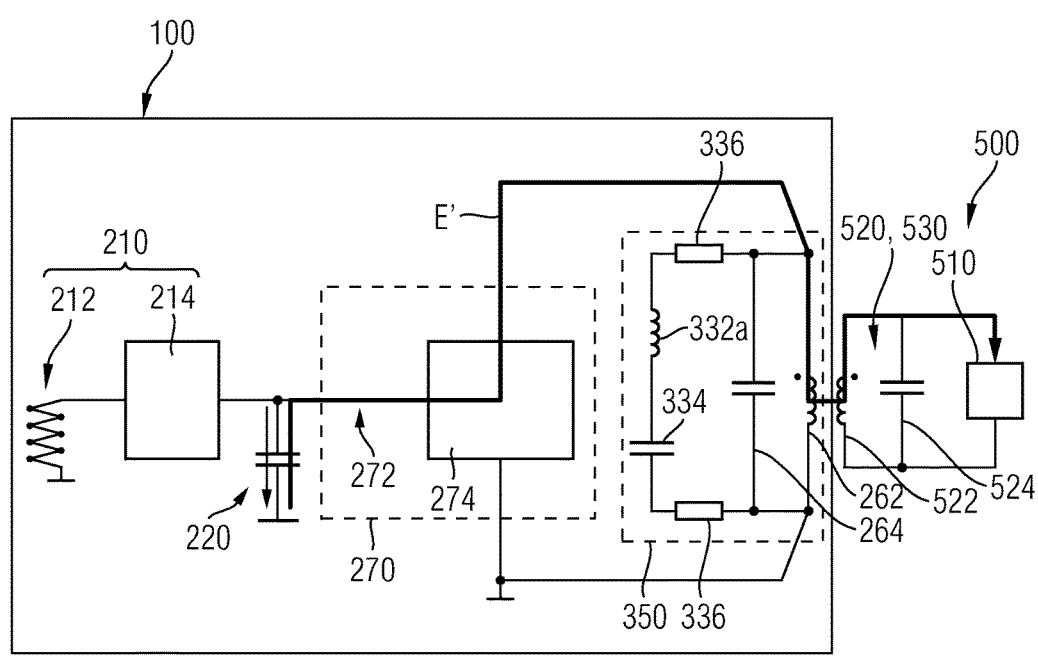
FIG. 10B is a schematic circuit diagram of a system for monitoring a body health parameter in a second modus.

260 of the functional skin patch 100, as already discussed with regard to FIG. 1B. In detail, the energy receiving unit 530 and the data transceiver unit 520 may use in common a coupling coil 522, as shown in FIGS. 10A and 10B. Furthermore, the implantable device 500 may comprise an energy storage unit 524, which may be a chargeable storage device. Herein, a silicon-based rechargeable lithium battery may be used. As silicon has highest lithium ion storage capacity/volume, even a very tiny-sized battery (A<1 mm$^2$) may provide storage capacity in the order to up to 250 to 500 µAh, which is sufficient for various applications. The energy storage unit 524 may further comprise a capacitor. Herein, printed energy storage devices or printed supercapacitors may be used.

A coupling coil 262 (FIGS. 10A and 10B) of the coupling antenna 260 and the coupling coil 522 of the implantable device 500 may comprise at least one of a radio frequency identification (RFID/nearfield communication (NFC) antenna). The diameter of the coupling coil 262 of the coupling antenna 260 may be in the range of 1 mm to 10 mm and the diameter of the antenna pattern 332 of the antenna layer 330 may be in a range of 1 cm to 10 cm. RFID devices operate at different radio frequency ranges, e.g. low frequency (LF) at about 28 to 136 kHz, high frequency (HF) at about 13.56 MHz, and ultra-high frequency (UHF) at 860 to 960 MHz. Each frequency range has unique characteristic in terms of RFID performance.

NFC is a short range technology that enables two devices to communicate when they are brought into actual touching distance. NFC enables sharing power and data using magnetic field induction at 13.56 MHz (HF) band, at short range, supporting varying data rates from 106 kbps, 212 kbps to 424 kbps. A key feature of NFC is that is allows two devices to interconnect. In reader/writer mode, an NFC tag is a passive device that stores data that can be read by an NFC enable device. In peer-to-peer mode, two NFC devices can exchange data. Bluetooth or WiFi link set up parameters can be shared using NFC and data such as virtual business cards or digital photos can be exchanged. In card emulation mode, the NFC device itself acts as an NFC tag, appearing to an external interrogator as a traditional contact less smart card. These NFC standards are acknowledged by major standardisation bodies and based on ISO/IEC 18092.

Passive UHF systems use propagation coupling, where an interrogator antenna emits electromagnetic energy radio frequency waves and the RFID tag receives the energy from the interrogator antenna, and the integrated circuit uses the energy to change the load on the antenna and reflect back an altered signal that is then demodulated. For the LF and HF RFID systems using interactive coupling, the range of the interrogator field is small (0.2 to 80 cm) and can be relatively easily controlled. UHF systems that use propagation coupling are harder to control, because energy is sent over long distances. The radio waves can reflect on hard surfaces and reach tags that are not in the normal range. LF and HF systems perform better than UHF systems around metal and water. The radio waves do reflect off metal and cause false reads, and they are better able to penetrate water. UHF radio waves are attenuated by water.

In addition, communication may be performed via any one of an Industrial, Scientific and Medical (ISM) Band, which operates in a frequency range between 6.765 MHz to 246 GHz and has bandwidths of up to 2 GHz.

The energy storage unit 524 is then configured to harvest energy from the coupling antenna 260 for charging the energy storage unit 524. The energy harvesting may be controlled by a processor unit.

The sensor unit 510 may be also configured to measure at least one body health parameter as already discussed above with regard to the sensor unit 240 of the functional skin patch 100. Furthermore, since the implantable device 500 is implanted in the body tissue, also invasive measurements like chemically analysing the interstitial fluid in the subcutaneous tissue may be performed. In addition, in case of implanting the implantable device 500 into a blood vessel, also blood pressure or blood flow may be measured by the implantable device 500, wherein the measured data is transmitted to the coupling antenna 260 and then via the antenna layer 330 to the external transceiver 600. The external transceiver 600 may be a mobile phone or a tablet PC being configured to communicate with the RF-circuit 230 of the functional skin patch 100 via the antenna pattern 332.

In the following, an employment of the functional skin patch 100 operating as a booster plaster in two different modes A and B will be described.

As shown in FIG. 10A, in a first mode A, at least one body health parameter is measured by the sensor unit 510 of the implantable device 500 only in a case, if an external RF-field of the external transceiver 600 is applied, which leads to a punctual measurement process. A continuous measurement over a predetermined time range (long term monitoring) requires a repeated application of the external RF-field from the external transceiver 600. Due to the provision of the thermo harvester 210 in the functional skin patch 100 according to an embodiment, the interface functionality of the functional skin patch 100 working as a booster plaster is enhanced by providing a local energy source within the functional skin patch 100. The temperature difference between the skin and the environment is converted into electric energy via the thermoelectric energy harvesting of the thermo harvester 210.

The locally generated energy is converted into an RF signal by a DC/AC transformer 274 and then applied to the coupling coil 262 of the coupling antenna 260 to be transferred to the implantable device 500. Therefore, the energizing unit 270 comprises the DC/AC-transformer 274, which is connected with the DC-terminal to the thermo harvester 210 and with the AC-terminal to the coupling antenna 260. The RF-signal triggers a measurement process of the implantable device 500. Thus, the functional unit 200 may further comprise a data storage unit 252 (cf. FIG. 5A and FIG. 6), wherein the functional unit 200 is configured to temporarily energize the implantable device 500, to receive measurement data transmitted from the implantable device 500, and to store the transmitted measurement data from the implantable device 500 in the data storage unit 252. The stored data in the data storage unit 252 may be stored for a predetermined time until the data storage unit 252 is read out by the external transceiver 600 on demand.

In the first modus A, which is illustrated in FIG. 10A, an external field is applied by the external transceiver 600, wherein the booster circuit of the functional skin patch 100 concentrates the field energy and transmits the concentrated field energy to the implantable device 500. The booster circuit 350 of the functional skin patch 100 comprises a coupling coil 332a of the antenna pattern 332, the coupling coil 262 of the coupling antenna 260, a first capacitor 334 and a second capacitor 264 for frequency tuning and intrinsic output resistances 336 mainly of the antenna unit 300. The power transmission from the external transceiver 600 through the booster circuit 350 to the implantable device 500 is illustrated by the arrow E in FIG. 10A.

The energizing field from the external transceiver 600 is further used for communication. Thus, the implantable device 500 is energized and at the same time the measurement data can be read out. Further, the implantable device 500 may be configured or a continuous measurement may be performed in case the external transceiver 600 is in constant reach of the functional skin patch 100, which may be the case for a smartphone constantly worn by a user wearing the functional skin patch 100 and the implantable device 500. In the first modus A, the local energy storage unit 220 is deactivated. Thus, in the first modus A, power transmission and data communication with extend range using the booster antenna of the interface plaster or functional skin patch 100 from an RF-reader is performed to achieve continuous measurement operation and data read-out from the sensors memory.

In the second modus B, as shown in FIG. 10B, the thermo harvester 210 generates local electric energy. The energy is temporarily stored and may be used on demand for energizing the implantable device 500. Therefore, an AC-signal is generated by the DC/AC-transformer 274 in predetermined repeated time ranges and directly applied to the coupling coil 262, as can be seen from the arrow E' in FIG. 10B. Since the larger coupling coil 332a of the antenna pattern 332 has higher intrinsic output resistances 336, the current is mainly flowing through the coupling coil 262 of the coupling antenna 260. A part of the energy is lost via the coupling coil 332a of the antenna pattern 332. The RF-field coupled into the implantable device 500 via the coupling coil 522 wakes the implantable device 500 up and triggers a measurement. The measurement result will be temporarily stored in the data storage unit 252, as described above. Thus, in the second modus B, a continuous power generation by the energy harvesting circuit to the energy storage is performed. Duty cycled activation of the DC/AC-transformer 274 is performed to transmit power to the implantable device 500 and to activate measurement operation. The result is stored internally in a non-volatile memory unit or data storage unit 252 until read-out using an RF-reader of the external transceiver 600. To perform the selective duty cycled activation of the implantable device 500, the energizing unit 270 further comprises a switch 272 to selectively connect the energizing unit 270 with the thermo harvester 210.

Thus, according to the embodiment of the functional skin patch 100 and the system for monitoring a body health parameter, continuous data logging of conventional implanted passive sensor grains using a smart booster antenna plaster may be achieved. In addition a maintenance free operation of the implanted sensor of the implantable device 500 may be achieved. Furthermore, direct RF-data communication via the booster antenna plaster or functional skin patch 100 using an external NFC device of the external transceiver 600 to read-out the measurement results is possible. A local (on-skin-power generation for trend measurements over the day without the need of an external field source leads to the possibility of performing a long term monitoring of body functions of a human or an animal for medical or scientific reasons.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A functional skin patch, comprising:
a first surface of the functional skin patch;
a second surface of the functional skin patch and opposite the first surface;
a functional unit disposed in the functional skin patch and comprising a thermo harvester, the thermo harvester having a first terminal thermally connected to the first surface and a second terminal; and
an antenna unit disposed in the functional skin patch and having a first terminal thermally connected to the second terminal of the thermo harvester and a second terminal thermally connected to the second surface,
wherein the antenna unit has a stacked layer structure comprising, in this sequence, a metal layer thermally connected to the second terminal of the thermo harvester, a ferrite layer thermally connected to the metal layer, and an antenna layer thermally connected to the ferrite layer.

2. The functional skin patch of claim 1, wherein the metal layer is a flexible metal foil having a thickness in a range between 5 μm and 1000 μm.

3. The functional skin patch of claim 1, wherein the ferrite layer is a flexible ferrite foil having a thickness in a range between 5 μm and 1000 μm.

4. The functional skin patch of claim 1, wherein the antenna layer includes an antenna pattern printed on the ferrite layer.

5. The functional skin patch of claim 1, wherein the metal layer, the ferrite layer, and the antenna layer are in direct contact with each other.

6. The functional skin patch of claim 1, wherein the antenna layer further comprises a metal dot layer printed on the ferrite layer for enhancing the surface area of the antenna layer.

7. The functional skin patch of claim 1, wherein the area of the first and the second surfaces of the functional skin patch are in a range of 20 $cm^2$ to 500 $cm^2$.

8. The functional skin patch of claim 1, further comprising:
a heat collector unit having a first terminal thermally connected to the first surface and a second terminal thermally connected to the first terminal of the thermo harvester; and
a thermally isolating layer,
wherein the thermo harvester is embedded in the thermally isolating layer.

9. The functional skin patch of claim 1, wherein the functional unit comprises an RF-circuit connected to the antenna layer via a connection plug extended through the metal layer and the ferrite layer.

10. The functional skin patch of claim 1, wherein the functional unit comprises a sensor unit configured to sense a body health parameter including at least one of a body temperature, a body pulse frequency, an electrocardiogram recording, an electro encephalogram recording, a body function, a blood sugar value, a blood pressure, and a blood heparin value.

11. The functional skin patch of claim 1, wherein the thermo harvester comprises an energy storage unit configured to store harvested body energy.

12. The functional skin patch of claim 1, wherein the functional unit comprises a processing unit configured to process measurement data of the sensor unit and transmit the measurement data to the RF-circuit.

13. The functional skin patch of claim 1, further comprising a coupling antenna configured to communicate with or energize an implantable device.

14. The functional skin patch of claim 13, wherein the antenna layer is connected to the coupling antenna so as to boost transmission from an external transceiver to the implantable device.

15. The functional skin patch of claim 13, wherein the functional unit comprises an energizing unit configured to energize the implantable device via the coupling antenna.

16. The functional skin patch of claim 15, wherein the energizing unit comprises a DC/AC-transformer having a DC-terminal connected to the thermo harvester and an AC-terminal connected to the coupling antenna.

17. The functional skin patch of claim 15, wherein the energizing unit comprises a switch configured to selectively connect the energizing unit with the thermo harvester.

18. The functional skin patch of claim 1, further comprising a data storage unit, wherein the functional unit is configured to temporarily energize the implantable device, to receive measurement data transmitted from the implantable device, and to store the transmitted measurement data from the implantable device in the data storage unit.

19. The functional skin patch of claim 1, wherein the thermo harvester comprises a Peltier element including $Bi_2Te_3$.

20. A system for monitoring a body health parameter, comprising:

an implantable device; and
a functional skin patch,
wherein the functional skin patch comprises a first surface, a second surface opposite the first surface, a functional unit comprising a thermo harvester having a first terminal thermally connected to the first surface and a second terminal, an antenna unit having a first terminal thermally connected to the second terminal of the thermo harvester and a second terminal thermally connected to the second surface, and a coupling antenna configured to communicate with or energize the implantable device,
wherein the antenna unit has a stacked layer structure comprising, in this sequence, a metal layer thermally connected to the second terminal of the thermo harvester, a ferrite layer thermally connected to the metal layer, and an antenna layer thermally connected to the ferrite layer,
wherein the implantable device comprises a sensor unit configured to measure at least one body health parameter, a data transceiver unit configured to transmit measurement data containing the at least one body health parameter to the functional skin patch, and an energy receiving unit configured to receive electromagnetic energy from the coupling antenna of the functional skin patch.

* * * * *